United States Patent
Hwang et al.

(10) Patent No.: US 11,618,012 B2
(45) Date of Patent: Apr. 4, 2023

(54) CATALYST FOR OXIDATIVE DEHYDROGENATION REACTION, AND METHOD FOR PRODUCING SAME

(71) Applicant: LG CHEM, LTD., Seoul (KR)

(72) Inventors: Ye Seul Hwang, Daejeon (KR); Dong Hyun Ko, Daejeon (KR); Joohyuck Lee, Daejeon (KR); Myungji Suh, Daejeon (KR)

(73) Assignee: LG CHEM, LTD., Seoul (KR)

( * ) Notice: Subject to any disclaimer, the term of this patent is extended or adjusted under 35 U.S.C. 154(b) by 354 days.

(21) Appl. No.: 16/963,639

(22) PCT Filed: Nov. 19, 2019

(86) PCT No.: PCT/KR2019/015836
§ 371 (c)(1),
(2) Date: Jul. 21, 2020

(87) PCT Pub. No.: WO2020/106013
PCT Pub. Date: May 28, 2020

(65) Prior Publication Data
US 2021/0060537 A1 Mar. 4, 2021

(30) Foreign Application Priority Data

Nov. 19, 2018 (KR) .................. 10-2018-0142601
Nov. 18, 2019 (KR) .................. 10-2019-0147776

(51) Int. Cl.
*B01J 23/889* (2006.01)
*B01J 21/12* (2006.01)
(Continued)

(52) U.S. Cl.
CPC .......... *B01J 23/8892* (2013.01); *B01J 21/12* (2013.01); *B01J 23/80* (2013.01); *B01J 23/862* (2013.01);
(Continued)

(58) Field of Classification Search
CPC ...... B01J 23/8892; B01J 23/80; B01J 23/862; B01J 21/12; B01J 35/08; B01J 37/0228;
(Continued)

(56) References Cited

U.S. PATENT DOCUMENTS

2009/0062588 A1   3/2009  Kowaleski
2010/0086832 A1   4/2010  Lopez et al.
(Continued)

FOREIGN PATENT DOCUMENTS

CN    101516550 A    8/2009
CN    101674883 A    3/2010
(Continued)

OTHER PUBLICATIONS

Machine translation of CN 107352991 A (Year: 2017).*
(Continued)

*Primary Examiner* — Coris Fung
*Assistant Examiner* — Catriona M Corallo
(74) *Attorney, Agent, or Firm* — Dentons US LLP

(57) ABSTRACT

Provided is a catalyst for an oxidative dehydrogenation reaction that comprises: a porous support; a core portion supported on the porous support and containing a first zinc ferrite-based catalyst; and a shell portion supported on the core portion and containing a second zinc ferrite-based catalyst, in which the first zinc ferrite-based catalyst and the second zinc ferrite-based catalyst are different from each other.

10 Claims, 1 Drawing Sheet

(51) Int. Cl.
*B01J 23/80* (2006.01)
*B01J 23/86* (2006.01)
*B01J 35/08* (2006.01)
*B01J 37/02* (2006.01)
*C07C 5/48* (2006.01)

(52) U.S. Cl.
CPC .......... *B01J 35/08* (2013.01); *B01J 37/0228* (2013.01); *B01J 37/0244* (2013.01); *C07C 5/48* (2013.01); *C07C 2521/04* (2013.01); *C07C 2523/06* (2013.01); *C07C 2523/26* (2013.01); *C07C 2523/34* (2013.01); *C07C 2523/80* (2013.01); *C07C 2523/86* (2013.01)

(58) Field of Classification Search
CPC .... B01J 37/0244; C07C 5/48; C07C 2521/04; C07C 2523/06; C07C 2523/26; C07C 2523/34; C07C 2523/80; C07C 2523/86
See application file for complete search history.

(56) References Cited

U.S. PATENT DOCUMENTS

| | | |
|---|---|---|
| 2010/0121123 A1 | 5/2010 | Chung et al. |
| 2011/0086295 A1 | 4/2011 | Lopez et al. |
| 2013/0158325 A1 | 6/2013 | Kwon et al. |
| 2014/0088331 A1 | 3/2014 | Rolland |
| 2014/0225024 A1 | 8/2014 | Kim et al. |
| 2018/0186711 A1 | 7/2018 | Suh et al. |
| 2018/0290126 A1 | 10/2018 | Kim et al. |
| 2018/0333702 A1 | 11/2018 | Suh et al. |
| 2019/0016649 A1* | 1/2019 | Kim .................. B01J 35/08 |
| 2019/0076836 A1 | 3/2019 | Byun et al. |
| 2019/0201876 A1 | 7/2019 | Suh et al. |
| 2019/0329226 A1 | 10/2019 | Suh et al. |

FOREIGN PATENT DOCUMENTS

| | | | | |
|---|---|---|---|---|
| CN | 103025425 A | | 4/2013 | |
| CN | 107206359 A | | 9/2017 | |
| CN | 107352991 A | * | 11/2017 | ........... C04B 35/265 |
| EP | 3269448 A2 | * | 1/2018 | ............. B01J 23/74 |
| EP | 3269448 A2 | | 1/2018 | |
| EP | 3437739 A2 | | 2/2019 | |
| JP | 2014-062094 | | 4/2014 | |
| JP | 2016-117057 | | 6/2016 | |
| KR | 10-2011-0078040 | | 7/2011 | |
| KR | 10-1064353 | | 9/2011 | |
| KR | 10-2013-0090241 | | 8/2013 | |
| KR | 10-1384650 | | 4/2014 | |
| KR | 10-2014-0098526 | | 8/2014 | |
| KR | 10-2017-0005724 | | 1/2017 | |
| KR | 10-2017-0068351 | | 6/2017 | |
| KR | 10-2017-0119051 | | 10/2017 | |
| KR | 10-2017-0138124 | | 12/2017 | |
| KR | 10-1854434 | | 5/2018 | |
| KR | 1854434 B1 | * | 5/2018 | ............. B01J 21/04 |
| KR | 10-2018-0115227 | | 10/2018 | |
| KR | 10-2018-0115228 | | 10/2018 | |
| WO | 2017-171441 | | 10/2017 | |

OTHER PUBLICATIONS

Lee, H. et al., "Oxidative Dehydrogenation of n-Butene to 1,3-Butadiene Over ZnMeIIIFeO4 Catalysts: Effect of Trivalent Metal (MeIII)," Catal. Lett. (2009) 131:344-349.

Qiu et al., "Effect of added Sb2O4, BiPO4 or SnO2 on the catalytic properties of ZnFe2O4 in the oxidative dehydrogenation of butene to butadiene," Applied Catalysis, 51(1): 235-253 (1989) (abstract only).

* cited by examiner

[Figure 1]
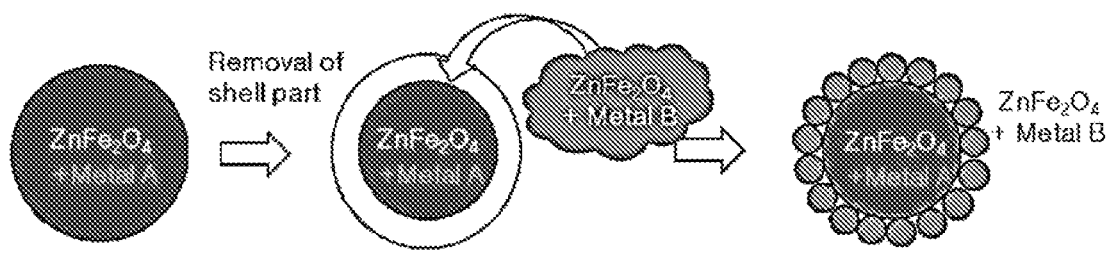
[Figure 2]
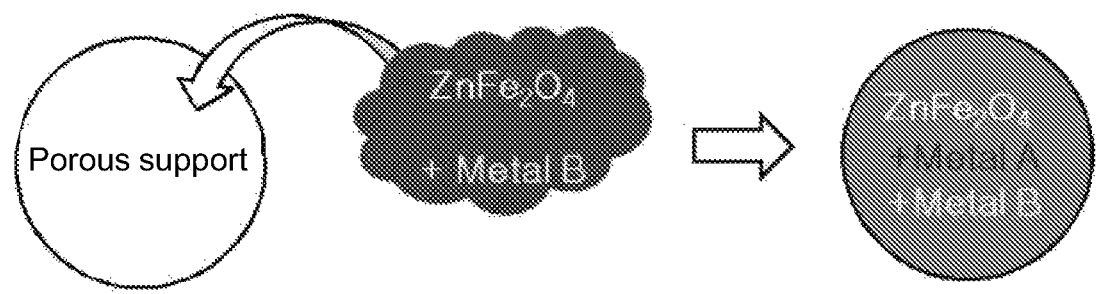

CATALYST FOR OXIDATIVE DEHYDROGENATION REACTION, AND METHOD FOR PRODUCING SAME

CROSS-REFERENCE TO RELATED APPLICATIONS

This application is a National Stage Application of International Application No. PCT/KR2019/015836 filed on Nov. 19, 2019, which claims priority to and the benefit of Korean Patent Application Nos. 10-2018-0142601 and 10-2019-0147776 filed in the Korean Intellectual Property Office on Nov. 19, 2018 and Nov. 18, 2019, respectively, the entire contents of which are incorporated herein by reference.

TECHNICAL FIELD

The present application relates to a catalyst for an oxidative dehydrogenation reaction and a method for producing the same.

BACKGROUND

An oxidative dehydrogenation reaction of butene for producing butadiene whose demand is gradually increasing in the petrochemical market is a reaction of producing butadiene and water by allowing butene and oxygen to react, and is thermodynamically advantageous and may lower the reaction temperature because stable water is produced as a product.

An oxidative dehydrogenation reaction of normal-butenes (1-butene, trans-2-butene, and cis-2-buitene) is a reaction of producing butadiene and water by allowing normal-butene and oxygen to react. However, many side reactions such as a complete oxidation reaction are expected because oxygen is used as a reactant in the oxidative dehydrogenation reaction, and as a result, it is the most important core technology to suppress such side reactions as much as possible and develop catalysts having high selectivity of butadiene. Examples of a catalyst used in the oxidative dehydrogenation reaction of butene, which has been known to date, comprise a ferrite-based catalyst, a tin-based catalyst, a bismuth molybdate-based catalyst, and the like.

Among them, the ferrite-based catalyst has different activities as a catalyst according to the type of metal constituting a divalent cation site of a spinel structure, and among them, zinc ferrite, magnesium ferrite, and manganese ferrite are known to show good activity for the oxidative dehydrogenation reaction of butene, and in particular, zinc ferrite has been reported to have higher selectivity of butadiene than other metal ferrite catalysts [F.-Y. Qiu, L.-T. Weng, E. Sham, P. Ruiz, B. Delmon, Appl. Catal., vol. 51, pp. 235 (1989)].

In the oxidative dehydrogenation reaction of butene, the utilization of a zinc ferrite-based catalyst has been reported, and in order to increase the reaction activity and service life of the zinc ferrite catalyst for the oxidative dehydrogenation reaction, it is known that butadiene can be obtained with a higher yield on a long term basis through a pretreatment and a post treatment such as treatment of a catalyst with an additive.

In the production of butadiene by the oxidative dehydrogenation of butene using a ferrite-based catalyst, an oxidative dehydrogenation reaction is conventionally performed under the conditions of steam which is present in a larger amount larger of 10 times or more than butene, and this is because steam is known to not only serve to lower the explosion range by reducing the partial pressure of butene, but also to be able to enhance the stability of a reaction vessel by removing reaction heat generated during the oxidative dehydrogenation reaction and increase the conversion of butene and increase the selectivity for butadiene by directly acting on the surface of the catalyst.

However, when steam is used in an amount larger than 10 times or more than butene, there is a problem in that the costs of steam itself are generated, and heat energy cannot be recovered by at least latent heat of water when the heat energy of a reactant comprising steam is recovered in the rear end of a reactor, and then the steam is compressed/cooled and condensed. Accordingly, when steam is used in large amounts in the oxidative dehydrogenation reaction process of butene, costs to use steam itself are high, and a lot of heat energy is lost, small amounts of oxygenates produced during the oxidative dehydrogenation reaction of butene are comprised in condensed water, so that costs of disposing a large amount of waste water are incurred, and as a result, the economic feasibility of the process cannot be secured.

For this reason, there is an urgent need for developing a catalyst capable of increasing the conversion and yield of butadiene and simultaneously enhancing the durability of the catalyst even under the conditions in which steam is used in small amounts so as to enhance the economic feasibility of the oxidative dehydrogenation process of butene.

BRIEF DESCRIPTION

Technical Problem

The present application has been made in an effort to provide a catalyst for an oxidative dehydrogenation reaction and a method for producing the same.

Technical Solution

An exemplary embodiment of the present application provides a catalyst for an oxidative dehydrogenation reaction, the catalyst comprising:

a core part comprising a porous support, and a first zinc ferrite-based catalyst supported on the porous support; and a shell part comprising a second zinc ferrite-based catalyst supported on the core part, in which the first zinc ferrite-based catalyst and the second zinc ferrite-based catalyst are different from each other.

Further, another exemplary embodiment of the present application provides a method for producing a catalyst for an oxidative dehydrogenation reaction, the method comprising:

forming a core part by supporting a first zinc ferrite-based catalyst on a porous support; and forming a shell part by supporting a second zinc ferrite-based catalyst on the core part, in which the first zinc ferrite-based catalyst and the second zinc ferrite-based catalyst are different from each other.

Further, still another exemplary embodiment of the present application provides a method for preparing butadiene, the method comprising:

preparing the catalyst for an oxidative dehydrogenation reaction; and producing butadiene using the catalyst for an oxidative dehydrogenation reaction in an oxidative dehydrogenation reaction of butene.

Advantageous Effects

A catalyst for an oxidative dehydrogenation reaction according to an exemplary embodiment of the present application can simultaneously introduce two effects of suppression of side reactions due to the introduction of metal components of the catalyst and a low hot spot movement speed without any change in structure of the ferrite by supporting two types of zinc ferrite-based catalysts on a porous support.

Further, the catalyst for an oxidative dehydrogenation reaction according to an exemplary embodiment of the present application can obtain butadiene with a high yield while using a small amount of steam.

Accordingly, the catalyst for an oxidative dehydrogenation reaction according to an exemplary embodiment of the present application can obtain a high yield of 1,3-butadiene and simultaneously have a low hot spot movement speed as compared to a zinc ferrite-based catalyst in the related art used for the oxidative dehydrogenation of butene.

BRIEF DESCRIPTION OF THE DRAWINGS

FIG. 1 is a view schematically illustrating a process of producing a catalyst for an oxidative dehydrogenation reaction according to an exemplary embodiment of the present application.

FIG. 2 is a view schematically illustrating a process of producing a catalyst for an oxidative dehydrogenation reaction in the related art.

DETAILED DESCRIPTION

Hereinafter, the present application will be described in more detail.

When one member is disposed "on" another member in the present specification, this comprises not only a case where the one member is brought into contact with another member, but also a case where still another member is present between the two members.

When one part "comprises" one constituent element in the present specification, unless otherwise specifically described, this does not mean that another constituent element is excluded, but means that another constituent element can be further comprised.

In the present specification, the "yield (%)" is defined as a value obtained by dividing the number of moles of 1,3-butadiene, which is a product of an oxidative dehydrogenation reaction, by the number of moles of butene which is a raw material. For example, the yield can be calculated using the following equation:

Yield (%)=[(the number of moles of 1,3-butadiene produced)/(the number of moles of butene supplied)]×100

In the present specification, the "conversion (%)" refers to a rate at which a reactant is converted into a product, and for example, the conversion of butene can be defined by the following equation:

Conversion (%)=[(the number of moles of butene reacted)/(the number of moles of butene supplied)]×100

In the present specification, the "selectivity (%)" is defined as a value obtained by dividing the change amount of butadiene (BD) by the change amount of butene (BE). For example, the selectivity can be calculated using the following equation:

Selectivity (%)=[(the number of moles of 1,3-butadiene or COx produced)/(the number of moles of butene reacted)]×100

In the specification, the "butadiene" means 1,3-butadiene.

As described above, a ferrite-based catalyst is usually used for a reaction of producing butadiene through the oxidative dehydrogenation reaction of butene. Among the ferrite-based catalysts, a zinc-ferrite catalyst is known to have the highest activity.

The zinc ferrite-based catalyst forms a spinel structure theoretically having a formula of $ZnFe_2O_4$, and it is possible to add an additional function to the catalyst using a method for adding a metal other than Zn and Fe. However, when a metal is added to a zinc ferrite catalyst, a phenomenon in which the inherent crystal structure of the zinc ferrite catalyst is changed occurs, and thus may instead lead to deterioration in performance of the catalyst.

Thus, the present inventors have conducted studies on a catalyst simultaneously comprising two or more types of a zinc ferrite catalyst to which a metal is added, a pure zinc ferrite catalyst to which no metal is added, and the like, thereby completing the present invention.

The catalyst for an oxidative dehydrogenation reaction according to an exemplary embodiment of the present application comprises: a core part comprising a porous support, and a first zinc ferrite-based catalyst supported on the porous support; and a shell part comprising a second zinc ferrite-based catalyst supported on the core part, in which the first zinc ferrite-based catalyst and the second zinc ferrite-based catalyst are different from each other.

In an exemplary embodiment of the present application, the first zinc ferrite-based catalyst and the second zinc ferrite-based catalyst can each independently be any one of the following Formulae 1 to 3. However, the first zinc ferrite-based catalyst and the second zinc ferrite-based catalyst are different from each other.

$$ZnFe_xO_y \quad \text{Formula 1}$$

$$(R1)_aZn_bFe_cO_y \quad \text{Formula 2}$$

$$(R2)_aZn_bFe_cO_{y'} \quad \text{Formula 3}$$

In Formulae 1 to 3,

R1 and R2 are each independently Cs, Ti, Zr, V, Nb, W, Cu, Ag, Cd, Sb, Ce, Cr, Mn, K, Co, or Mo, provided that R1 and R2 are different from each other, x is each independently 1 to 2.8, y and y' are each independently 1 to 6, and a, b, c, a', b', and c' are each independently more than 0 and 2.8 or less.

In an exemplary embodiment of the present application, the first zinc ferrite-based catalyst can be of Formula 1, and the second zinc ferrite-based catalyst can be of Formula 2.

Further, in an exemplary embodiment of the present application, the second zinc ferrite-based catalyst can be of Formula 1, and the first zinc ferrite-based catalyst can be of Formula 2.

In addition, in an exemplary embodiment of the present application, the first zinc ferrite-based catalyst can be of Formula 2, and the second zinc ferrite-based catalyst can be of Formula 3.

In an exemplary embodiment of the present application, different catalysts were intended to be each supported inside and outside the porous support. That is, a core part was formed by supporting a first zinc ferrite-based catalyst inside a porous support and a shell part was formed by supporting a second zinc ferrite-based catalyst different from the first zinc ferrite-based catalyst outside the porous support. Accordingly, it is possible to provide a catalyst for an oxidative dehydrogenation reaction, which can suppress side reactions and has a low hot spot movement speed.

Accordingly, in an exemplary embodiment of the present application, the first zinc ferrite-based catalyst can be supported inside the porous support, and the second zinc ferrite-based catalyst can be supported on the outermost surface of the porous support.

In an exemplary embodiment of the present application, a content of the first zinc ferrite-based catalyst can be 5 wt % to 40 wt %, and 15 wt % to 30 wt %, based on a total weight of the catalyst for an oxidative dehydrogenation reaction. When the content of the first zinc ferrite-based catalyst is less than 5 wt %, the process cost due to an increase in reaction temperature can be increased, and when the content is more than 40 wt %, an increase in COx selectivity and a decrease in conversion due to an increase in heat generation of the catalyst can occur.

In an exemplary embodiment of the present application, a content of the second zinc ferrite-based catalyst can be 0.1 wt % to 30 wt %, and can be 10 wt % to 20 wt %, based on the total weight of the catalyst for an oxidative dehydrogenation reaction. When the content of the second zinc ferrite-based catalyst is less than 0.1 wt %, the effect may not be obtained as compared to when the second zinc ferrite-based catalyst is not introduced, and when the content is more than 30 wt %, the loss of the catalyst during the production process can occur due to the abrasion of the catalyst.

In an exemplary embodiment of the present application, the catalyst for an oxidative dehydrogenation reaction can further comprise an organic binder in addition to the first zinc ferrite-based catalyst and the second zinc ferrite-based catalyst. For example, the organic binder can be ethyl cellulose, methyl cellulose, or a derivative thereof, and can be preferably methyl cellulose, but is not limited thereto. The organic binder can improve the coatability and moldability of the catalyst and can alleviate the generation of cracks in the drying step of the catalyst production process.

In an exemplary embodiment of the present application, the porous support can comprise a plurality of pores formed inside thereof and on the surface thereof, and in this case, the porous support can have a porosity of 70 vol % or less, specifically, 50 vol % or less, and more specifically 30 vol % or less. When the porous support has a porosity of more than 70 vol %, the catalyst supported in any region inside the porous support may not participate in the reaction, and an unnecessary side reaction can occur because it is difficult to disperse heat generation during the reaction.

In an exemplary embodiment of the present application, the shape of the porous support is not particularly limited, but can comprise one or more of a spherical shape, a cylindrical shape, a cyclic shape, and a plate shape.

In an exemplary embodiment of the present application, the porous support can comprise one or more of alumina, silica, zirconia, silicon carbide, and cordierite, and can be specifically alumina.

Further, the method for producing a catalyst for an oxidative dehydrogenation reaction according to an exemplary embodiment of the present application comprises: forming a core part by supporting a first zinc ferrite-based catalyst on a porous support; and forming a shell part by supporting a second zinc ferrite-based catalyst on the core part, in which the first zinc ferrite-based catalyst and the second zinc ferrite-based catalyst are different from each other.

In the method for producing a catalyst for an oxidative dehydrogenation reaction according to an exemplary embodiment of the present application, the contents on the first zinc ferrite-based catalyst, the second zinc ferrite-based catalyst, and the porous support are the same as those described above.

The method for producing a catalyst for an oxidative dehydrogenation reaction according to an exemplary embodiment of the present application can additionally comprise preparing each the first zinc ferrite-based catalyst and the second zinc ferrite-based catalyst.

The first zinc ferrite-based catalyst and the second zinc ferrite-based catalyst can be of any one of Formulae 1 to 3 as described above, and can use a method for producing a zinc ferrite-based catalyst known in the art.

For example, the method for producing the zinc ferrite-based catalyst of Formula 1 can comprise: obtaining a precipitate by bringing a metal precursor solution comprising a zinc precursor, a ferrite precursor, and water into contact with an aqueous basic solution; and filtering the precipitate, and then drying the filtered precipitate, and firing the dried precipitate.

In an exemplary embodiment of the present application, the zinc precursor and the ferrite precursor can be each independently one or more selected from the group consisting of nitrate, ammonium salt, sulfate, and chloride, or a hydrate thereof. Specifically, it is preferred that the zinc precursor and the ferrite precursor are nitrate or chloride, or a hydrate thereof.

In an exemplary embodiment of the present application, the zinc precursor can be zinc chloride ($ZnCl_2$). In this case, the formation of the zinc ferrite-based catalyst is excellent.

In an exemplary embodiment of the present application, the ferrite precursor can be ferric chloride ($FeCl_3$). In this case, the formation of the zinc ferrite-based catalyst is excellent.

In an exemplary embodiment of the present application, the water can use pure water (DI water), distilled water, and the like. The temperature of the water can be more than 0° C. and 40° C. or less. The temperature of the water can be preferably more than 0° C. and 30° C. or less. The temperature of the water can be more preferably 5° C. to 25° C. When the temperature of the water satisfies the above range, an amount of catalyst produced by the precipitation method can be increased, and the improvement in selectivity and yield of butadiene caused by the oxidative dehydrogenation reaction can be ultimately brought about by adjusting the content of the active catalyst.

In an exemplary embodiment of the present application, a pH of the aqueous basic solution can be 7 to 10. Preferably, the pH can be 7.5 to 9. When the pH satisfies the above range, there is an effect of stably producing the zinc ferrite catalyst.

In an exemplary embodiment of the present application, the aqueous basic solution can be one or more selected from the group consisting of potassium hydroxide, ammonium carbonate, ammonium bicarbonate, an aqueous sodium hydroxide solution, an aqueous sodium carbonate solution, and ammonium water. Preferably, the aqueous basic solution can be ammonia water. In this case, in the process of producing a zinc ferrite-based catalyst, there is an effect that facilitates precipitation, and thus makes the formation of catalyst particles excellent.

In an exemplary embodiment of the present application, a concentration of the aqueous basic solution can be 20 wt % to 40 wt %, and can be 25 wt % to 30 wt %.

In an exemplary embodiment of the present application, the obtaining of the precipitate can further comprise bringing the metal precursor solution into contact with the basic aqueous solution, and then stirring the resulting solution. The formation of precipitations of metal precursors is facilitated by further comprising the stirring of the resulting solution, so that catalyst particles are favorably formed. The stirring of the resulting solution can be performed at room temperature, and the method for stirring the resulting solution can be used without limitation as long as the method mixes a liquid with a liquid. Further, the stirring time of the stirring of the resulting solution can be 30 minutes to 3 hours, and can be 1 hour to 2 hours.

In an exemplary embodiment of the present application, the filtering of the precipitate is not particularly limited as long as the method is a filtration method typically used in the art. For example, the method can be vacuum filtration. Specifically, the method can be a method of filtering the precipitate by using a vacuum pump to reduce pressure, and in this case, there is an effect that separates the catalyst from washing liquid and moisture.

In an exemplary embodiment of the present application, the method can further comprise washing the precipitate before the precipitate is filtered and then fired. Unnecessary ions remaining in the precipitate can be removed by further comprising the washing of the precipitate.

In an exemplary embodiment of the present application, the drying of the precipitate can be performed before the precipitate is fired after the precipitate is filtered and then washed. The drying of the precipitate is not particularly limited as long as the drying method is typically used in the art. For example, a dryer can be used, and an oven can be used. The drying of the precipitate can be performed at 80° C. to 150° C.

In an exemplary embodiment of the present application, the firing of the precipitate can include increasing the temperature from 80° C. and a rate of 1° C./min and maintaining the temperature at 600° C. to 800° C. for 5 hours to 10 hours. In the firing of the precipitate, the precipitate can be fired specifically at 600° C. to 700° C., and more specifically at 600° C. to 650° C. In the firing of the precipitate, the precipitate can be fired specifically for 5 hours to 8 hours, and more specifically for 5 hours to 6 hours.

The method for firing the precipitate can be a heat treatment method typically used in the art.

In an exemplary embodiment of the present application, the firing of the precipitate can be performed by injecting air at 1 L/min into a firing furnace.

The method for producing a catalyst for an oxidative dehydrogenation reaction according to an exemplary embodiment of the present application comprises forming a core part by supporting a first zinc ferrite-based catalyst on a porous support. The forming of the core part by supporting the first zinc ferrite-based catalyst on the porous support can comprise coating the inside and the entire outermost surface of the porous support with the first zinc ferrite-based catalyst.

Further, the method for producing a catalyst for an oxidative dehydrogenation reaction according to an exemplary embodiment of the present application comprises forming a shell part by supporting a second zinc ferrite-based catalyst on the core part. The forming of the shell part by supporting the second zinc ferrite-based catalyst on the core part can comprise: removing the first zinc ferrite-based catalyst provided on the outermost surface of the porous support; and coating the outermost surface of the porous support with the second zinc ferrite-based catalyst.

In addition, in an exemplary embodiment of the present application, the removing of the first zinc ferrite-based catalyst provided on the outermost surface of the porous support can be performed until an amount of first zinc ferrite-based catalyst removed becomes 0.1 wt % to 5 wt % based on the total weight of the coated first zinc ferrite-based catalyst, and can be performed until the amount becomes 0.15 wt % to 4.5 wt %. When the amount of first zinc ferrite-based catalyst removed is less than 0.1 wt %, the loss due to abrasion can occur during the process of supporting the second zinc ferrite-based catalyst, and when the amount is more than 5 wt %, the amount of first zinc ferrite-based catalyst removed is increased, so that the cost of producing the catalyst can be increased.

In an exemplary embodiment of the present application, the method for removing the first zinc ferrite-based catalyst provided on the outermost surface of the porous support can be performed by a method for putting a catalyst supported by the first zinc ferrite-based catalyst into a 100 μm sieve and applying vibration to the sieve for approximately 10 minutes to 1 hour. For example, when the sieving is performed for 10 minutes, about 0.1 wt % can be removed.

The process of producing a catalyst for an oxidative dehydrogenation reaction according to an exemplary embodiment of the present application is schematically illustrated in the following FIG. 1, and the process of producing a catalyst for an oxidative dehydrogenation reaction in the related art is schematically illustrated in FIG. 2. As in the following FIG. 1, in an exemplary embodiment of the present application, the first zinc ferrite-based catalyst can be supported inside the porous support, and the second zinc ferrite-based catalyst can be supported on the outermost surface of the porous support.

Further, an exemplary embodiment of the present application provides a method for producing butadiene, the method comprising: preparing the catalyst for an oxidative dehydrogenation reaction; and producing butadiene by using the catalyst for an oxidative dehydrogenation reaction in an oxidative dehydrogenation reaction of butene.

In an exemplary embodiment of the present application, the producing of the butadiene can allow a raw material comprising C4 fractions, steam, oxygen ($O_2$), and nitrogen ($N_2$) to react under the conditions of a reaction temperature of 250° C. to 500° C., a pressure condition of 0.1 bar to 10 bar, and a gas hourly space velocity (GHSV) of 100 $h^{-1}$ to 400 $h^{-1}$.

The C4 fractions can mean C4 raffinate-1,2,3 remaining by separating useful compounds from a C4 mixture produced by naphtha cracking, and can mean C4 classes which can be obtained through ethylene dimerization.

In an exemplary embodiment of the present application, the C4 fractions can be one or a mixture of two or more selected from the group consisting of n-butane, trans-2-butene, cis-2-butene, and 1-butene.

In an exemplary embodiment of the present application, the steam or nitrogen ($N_2$) is a diluted gas introduced for the purpose of reducing the explosion danger of the reactant, preventing coking of the catalyst, removing the reaction heat, and the like, in the oxidative dehydrogenation reaction.

In an exemplary embodiment of the present application, the oxygen ($O_2$) is an oxidant and reacts with C4 fractions to cause a dehydrogenation reaction.

In an exemplary embodiment of the present application, the oxidative dehydrogenation reaction can be performed according to the following Reaction Formula 1 or Reaction Formula 2.

$$C_4H_8 + \tfrac{1}{2}O_2 \rightarrow C_4H_6 + H_2O \qquad \text{Reaction Formula 1}$$

$$C_4H_{10} + O_2 \rightarrow C_4H_6 + 2H_2O \qquad \text{Reaction Formula 2}$$

Hydrogen of butane or butene is removed by the oxidative dehydrogenation reaction, and as a result, butadiene is produced. Meanwhile, the oxidative dehydrogenation reaction can produce a side reaction product comprising carbon monoxide (CO), carbon dioxide ($CO_2$), or the like, in addition to the main reaction such as Reaction Formula 1 or 2. The oxidative dehydrogenation reaction can comprise a process in which the side reaction product is separated so as not to be continuously accumulated in the process, and is released out of the system.

According to an exemplary embodiment of the present application, in the method for preparing butadiene, the conversion of butene can be 72% or more, preferably 72.5% or more, and more preferably 79% or more.

According to an exemplary embodiment of the present specification, in the method for producing butadiene, the selectivity of butadiene can be 85% or more, preferably 85.8% or more, and more preferably 87% or more.

As described above, the catalyst for an oxidative dehydrogenation reaction according to an exemplary embodiment of the present application can simultaneously introduce two effects of suppression of side reactions due to the introduction of metal components of the catalyst and a low hot spot movement speed without any change in structure of the ferrite by supporting two types of zinc ferrite-based catalysts on a porous support.

Further, the catalyst for an oxidative dehydrogenation reaction according to an exemplary embodiment of the present application can obtain butadiene with a high yield while using a small amount of steam.

Accordingly, the catalyst for an oxidative dehydrogenation reaction according to an exemplary embodiment of the present application can obtain a high yield of 1,3-butadiene and simultaneously have a low hot spot movement speed as compared to a zinc ferrite-based catalyst in the related art used for the oxidative dehydrogenation of butene.

Mode for Practicing the Invention

Hereinafter, the present application will be described in detail with reference to Examples for specifically describing the present application. However, the Examples according to the present application can be modified in various forms, and it is not interpreted that the scope of the present application is limited to the Examples described in detail below. The Examples of the present application are provided for more completely explaining the present application to the person with ordinary skill in the art.

EXAMPLES

Comparative Example 1

A metal precursor solution was prepared by dissolving 12.019 g of zinc chloride ($ZnCl_2$) and 47.662 g of ferric chloride ($FeCl_3$) in 155.59 g of distilled water. In this case, for a molar ratio of the metal components comprised in the metal precursor solution, Zn:Fe was 1:2. An aqueous ammonia solution was added dropwise to the prepared aqueous metal precursor solution such that the pH was 9, and the resulting solution was stirred for 1 hour and co-precipitated. Thereafter, a co-precipitate was obtained by filtering the co-precipitation solution under reduced pressure, and after the co-precipitate was dried at 90° C. for 16 hours, and then the temperature was increased up to 650° C. at a warming rate of 1° C./min at 80° C. under air atmosphere, a zinc-iron oxide ($ZnFe_2O_4$) powder having a spinel structure was produced by maintaining the temperature for 6 hours.

A catalyst slurry was produced by pulverizing the produced metal oxide powder to 0.6 mm to 0.85 mm and diluting the pulverized metal oxide powder in water at a weight ratio of 1:1. A binder for increasing the strength was added to the catalyst slurry, if necessary. A porous aluminum silicate support was immersed in the produced catalyst slurry, and the resulting mixture was aerated, and then dried at 120° C. for 1 hour. Thereafter, the process of immersing the dried porous aluminum silicate support again in the catalyst slurry, and aerating and then drying the resulting mixture was repeated three times. A catalyst for an oxidative dehydrogenation reaction having a porous structure was produced by drying the thus obtained catalyst at 120° C. for 16 hours, increasing the temperature up to 650° C. at a warming rate of 1° C./min at 80° C. under air atmosphere, and then maintaining the temperature for 6 hours.

Comparative Example 2

A catalyst for an oxidative dehydrogenation reaction was produced in the same manner as in Comparative Example 1, except that in Comparative Example 2, 0.35 g of manganese chloride ($MnCl_2.4H_2O$) was additionally introduced during the preparation of the metal precursor solution.

Comparative Example 3

A catalyst for an oxidative dehydrogenation reaction was produced in the same manner as in Comparative Example 1, except that in Comparative Example 3, 0.35 g of chromium nitrate ($Cr(NO_3)_3.9H_2O$) was additionally introduced during the preparation of the metal precursor solution.

Comparative Example 4

A catalyst for an oxidative dehydrogenation reaction was produced in the same manner as in Comparative Example 1, except that in Comparative Example 4, 0.35 g of manganese chloride ($MnCl_2.4H_2O$) and 0.35 g of chromium nitrate ($Cr(NO_3)_3.9H_2O$) were additionally introduced during the production of the catalyst slurry.

Example 1

1) Production of Core Part

A metal precursor solution was prepared by dissolving 12.019 g of zinc chloride ($ZnCl_2$), 47.662 g of ferric chloride ($FeCl_3$), and 0.35 g of manganese chloride ($MnCl_2.4H_2O$) in 155.59 g of distilled water. In this case, for a molar ratio of the metal components comprised in the metal precursor solution, Zn:Fe:Mn was 1:2:0.02. An aqueous ammonia solution was added dropwise to the prepared aqueous metal precursor solution such that the pH was 9, and the resulting solution was stirred for 1 hour and co-precipitated. Thereafter, a co-precipitate was obtained by filtering the co-precipitation solution under reduced pressure, and after the co-precipitate was dried at 90° C. for 16 hours, and then the temperature was increased up to 650° C. at a warming rate of 1° C./min from 80° C. under air atmosphere, a zinc-iron-manganese oxide powder having a spinel structure was produced by maintaining the temperature for 6 hours.

A first zinc ferrite-based catalyst slurry was produced by pulverizing the produced metal oxide powder to 0.6 mm to 0.85 mm and diluting the pulverized metal oxide powder in water at a weight ratio of 1:1. A binder for increasing the strength was added to the catalyst slurry, if necessary. A porous aluminum silicate support was immersed in the produced first zinc ferrite-based catalyst slurry, and the resulting mixture was aerated, and then dried at 120° C. for 1 hour. Thereafter, the process of immersing the dried porous aluminum silicate support again in the first zinc ferrite-based catalyst slurry, and aerating and then drying the resulting mixture was repeated three times. The thus obtained catalyst was dried at 120° C. for 16 hours.

2) Production of Shell Part

Thereafter, 3.2 g of the first zinc ferrite-based catalyst provided on the outermost surface of the porous aluminum silicate support was removed using a method for putting a catalyst supported by the first zinc ferrite-based catalyst into a 100 μm sieve and applying vibration to the sieve. In this case, an amount of first zinc ferrite-based catalyst removed was 0.15 wt % based on a total weight of the coated first zinc ferrite-based catalyst.

A metal precursor solution was prepared by dissolving 12.019 g of zinc chloride ($ZnCl_2$), 47.662 g of ferric chloride ($FeCl_3$), and 0.35 g of chromium nitrate ($Cr(NO_3)_3.9H_2O$) in 155.59 g of distilled water. In this case, for a molar ratio of the metal components comprised in the metal precursor solution, Zn:Fe:Cr was 1:2:0.01. An aqueous ammonia solution was added dropwise to the prepared aqueous metal precursor solution such that the pH was 9, and the resulting solution was stirred for 1 hour and co-precipitated. Thereafter, a co-precipitate was obtained by filtering the co-precipitation solution under reduced pressure, and after the co-precipitate was dried at 90° C. for 16 hours, and then the temperature was increased up to 650° C. at a warming rate of 1° C./min from 80° C. under air atmosphere, a zinc-iron-chromium oxide powder having a spinel structure was produced by maintaining the temperature for 6 hours.

A second zinc ferrite-based catalyst slurry was produced by pulverizing the produced zinc-iron-chromium oxide powder to 0.6 mm to 0.85 mm and diluting the pulverized metal oxide powder in water at a weight ratio of 1:1. A porous aluminum silicate support in which the first zinc ferrite-based catalyst on the outermost surface had been removed was immersed in the produced second zinc ferrite-based catalyst slurry, and the resulting mixture was aerated, and then dried at 120° C. for 1 hour. Thereafter, the process of immersing the dried porous aluminum silicate support again in the second zinc ferrite-based catalyst slurry, and aerating and then drying the resulting mixture was repeated three times. A catalyst for an oxidative dehydrogenation reaction having a porous structure was produced by drying the thus obtained catalyst at 120° C. for 16 hours.

The analysis of contents of Fe, Zn, Mn, Cr, and the like in the catalysts for an oxidative dehydrogenation reaction produced in the Examples and the Comparative Examples can be performed using an inductively coupled plasma (ICP) analysis. The ICP analysis can be measured using an inductively coupled plasma-optical emission (ICP-OES) apparatus. More specifically, an ICP-OES (Optima 7300DV) device can be used, and the procedure is as follows.

1) About 0.1 g of a sample is accurately measured in a vial.

2) About 1 mL of concentrated sulfuric acid is put into the vial containing the sample.

3) The sample is carbonized by heating the sample on a hot plate.

4) The sample is allowed to react while adding a small amount of nitric acid thereto in order to promote an oxidation reaction.

5) The color of the solution is changed from dark black to light yellow by repeating the foregoing process.

6) When the sample is completely dissolved to be clear, the sample is diluted with ultrapure water so as to have a volume of 10 mL.

7) The solution is filtered and analyzed by ICP-OES.

8) ICP-OES analysis conditions

RF power(W): 1300

Torch Height(mm): 15.0

Plasma Gas Flow(L/min): 15.00

Sample Gas Flow(L/min): 0.8

Aux. Gas flow(L/min): 0.20

Pump Speed(mL/min): 1.5

Internal Standard: Y or Sc

<Experimental Example> Production of butadiene

In a metal tubular reactor having a diameter of 1.8 cm as a reactor, the catalyst for an oxidative dehydrogenation reaction produced in each of the Examples and the Comparative Examples was fixed as a catalyst layer volume of 150 cc, a 2-butene mixture of 40 wt % of cis-2-butene and 60 wt % of trans-2-butene as a reactant and oxygen were used, and nitrogen and steam were fed thereto. The ratio of the reactants was set at a molar ratio of oxygen/butene 0.67, steam/butene 5, and nitrogen/butene 2.67, and steam obtained by vaporizing water in a vaporizer at 360° C. was fed along with the reactants to the reactor.

The amount of the butene mixture was controlled at 0.625 cc/min using a mass flow controller for liquids, oxygen and nitrogen were controlled using a mass flow controller for gases, and for the amount of steam, the injection speed was controlled using a liquid pump. The gas hourly space velocity (GHSV) of the reactor was set at 120 $h^{-1}$, and the reactants were allowed to react under the temperature conditions shown in the following Table 1 at normal pressure (pressure gauge 0).

The butene conversion, butadiene selectivity, butadiene yield (Y), and COx selectivity were calculated by performing a gas chromatography (GC) analysis from the products after the reaction, and the hot spot temperature and movement speed were measured by connecting a thermo-couple (TC) to a transfer device, and scanning the reactor while moving the transfer device at an equal speed from the top of the reactor to the end of the reactor.

<GC Analysis Conditions>

① Column: HP-1 (L: 30 m, ID: 0.32 mm, film: 1.05 m)

② Injection volume: 1 μl

③ Inlet Temp.: 280° C., Pressure: 36.3 psi, Total flow: 33.5 ml/min, Split flow: 30 ml/min, split ratio: 20.5:1

④ Column flow: 1.2 ml/min

⑤ Oven temp.: 50° C.→0° C. (6 min), 0° C. (maintained for 15 min), 0° C.→250° C. temperature increased and maintained (40 min)

⑥ Detector temp.: 280° C., Hz: 35 ml/min, Air: 300 ml/min, He: 20 ml/min

⑦ GC Model: Agilent 6890

TABLE 1

| | Hot spot Temperature (° C.) | Hot spot Movement speed (mm/hr) | Butene Conversion (%) | Butadiene Selectivity (%) | COx Selectivity (%) |
|---|---|---|---|---|---|
| Example 1 | 505 | 0.35 | 82.0 | 91.1 | 8.1 |
| Comparative Example 1 | 559 | 0.85 | 78.2 | 83.6 | 15.3 |
| Comparative Example 2 | 533 | 0.09 | 81.1 | 85.2 | 13.9 |
| Comparative Example 3 | 504 | 0.85 | 83.2 | 88.3 | 10.9 |

TABLE 1-continued

| | Hot spot Temperature (° C.) | Hot spot Movement speed (mm/hr) | Butene Conversion (%) | Butadiene Selectivity (%) | COx Selectivity (%) |
|---|---|---|---|---|---|
| Comparative Example 4 | 482 | 1.64 | 90.1 | 87.7 | 11.4 |

As shown in the results above, a catalyst for an oxidative dehydrogenation reaction according to an exemplary embodiment of the present application can simultaneously introduce two effects of suppression of side reactions due to the introduction of metal components of the catalyst and a low hot spot movement speed without any change in structure of the ferrite by supporting two types of zinc ferrite-based catalysts on a porous support.

Further, the catalyst for an oxidative dehydrogenation reaction according to an exemplary embodiment of the present application can obtain butadiene with a high yield while using a small amount of steam.

Accordingly, the catalyst for an oxidative dehydrogenation reaction according to an exemplary embodiment of the present application can obtain a high yield of 1,3-butadiene and simultaneously have a low hot spot movement speed as compared to a zinc ferrite-based catalyst in the related art used for the oxidative dehydrogenation of butene.

The invention claimed is:

1. A catalyst for an oxidative dehydrogenation reaction, the catalyst comprising:
   a core part comprising a porous support, and a first zinc ferrite-based catalyst supported on the porous support; and
   a shell part comprising a second zinc ferrite-based catalyst supported on the core part,
   wherein the first zinc ferrite-based catalyst and the second zinc ferrite-based catalyst are different from each other, and
   wherein the first zinc ferrite-based catalyst has the following Formula 2 and the second zinc ferrite-based catalyst has the following Formula 3:

$(R1)_a Zn_b Fe_c O_y$ <span></span> Formula 2

$(R2)_{a'} Zn_{b'} Fe_{c'} O_{y'}$ <span></span> Formula 3 wherein in Formulae 2 and 3:
   R1 and R2 are each independently Cs, Ti, Zr, V, Nb, W, Cu, Ag, Cd, Sb, Ce, Cr, Mn, K, Co, or Mo, provided that R1 and R2 are different from each other;
   y and y' are each independently 1 to 6; and
   a, b, c, a', b', and c' are each independently more than 0 and 2.8 or less.

2. The catalyst of claim 1, wherein a content of the first zinc ferrite-based catalyst is 5 wt % to 40 wt %, based on a total weight of the catalyst.

3. The catalyst of claim 1, wherein a content of the second zinc ferrite-based catalyst is 0.1 wt % to 30 wt %, based on a total weight of the catalyst.

4. The catalyst of claim 1, wherein a shape of the porous support comprises one or more shapes selected from the group consisting of a spherical shape, a cylindrical shape, a cyclic shape, and a plate shape.

5. The catalyst of claim 1, wherein the porous support comprises one or more of alumina, silica, zirconia, silicon carbide, and cordierite.

6. A method for producing a catalyst for an oxidative dehydrogenation reaction, the method comprising:
   forming a core part by supporting a first zinc ferrite-based catalyst on a porous support; and
   forming a shell part by supporting a second zinc ferrite-based catalyst on the core part,
   wherein the first zinc ferrite-based catalyst and the second zinc ferrite-based catalyst are different from each other, and wherein the first zinc ferrite-based catalyst has the following Formula 2 and the second zinc ferrite-based catalyst has the following Formula 3:

$(R1)_a Zn_b Fe_c O_y$ <span></span> Formula 2

$(R2)_{a'} Zn_{b'} Fe_{c'} O_{y'}$ <span></span> Formula 3 wherein in Formulae 2 and 3:
   R1 and R2 are each independently Cs, Ti, Zr, V, Nb, W, Cu, Ag, Cd, Sb, Ce, Cr, Mn, K, Co, or Mo, provided that R1 and R2 are different from each other;
   y and y' are each independently 1 to 6; and
   a, b, c, a', b', and c' are each independently more than 0 and 2.8 or less.

7. The method of claim 6, wherein the forming of the core part by supporting the first zinc ferrite-based catalyst on the porous support comprises:
   coating the inside and the entire outermost surface of the porous support with the first zinc ferrite-based catalyst.

8. The method of claim 7, wherein the forming of the shell part by supporting the second zinc ferrite-based catalyst on the core part comprises:
   removing the first zinc ferrite-based catalyst provided on the outermost surface of the porous support; and coating the outermost surface of the porous support with the second zinc ferrite-based catalyst.

9. The method of claim 8, wherein the removing of the first zinc ferrite-based catalyst provided on the outermost surface of the porous support is performed until an amount of first zinc ferrite-based catalyst removed becomes 0.1 wt % to 5 wt % based on the total weight of the coated first zinc ferrite-based catalyst.

10. A method for producing butadiene, the method comprising:
   preparing the catalyst for an oxidative dehydrogenation reaction of claim 1; and
   producing butadiene using the catalyst for an oxidative dehydrogenation reaction in an oxidative dehydrogenation reaction of a butene by allowing a raw material comprising C4 fractions containing a butene, steam, oxygen ($O_2$), and nitrogen ($N_2$), to react at a reaction temperature of 250° C. to 500° C., a pressure of 0.1 bar to 10 bar, and a gas hourly space velocity (CHSV) of 100 $h^{-1}$ to 400 $h^{-1}$.

* * * * *